United States Patent
Dijkstra

(10) Patent No.: US 11,931,093 B2
(45) Date of Patent: Mar. 19, 2024

(54) HIGH-FREQUENCY GENERATOR, CONTROL UNIT, METHOD FOR OPERATING A HIGH-FREQUENCY GENERATOR

(71) Applicant: OLYMPUS WINTER & IBE GMBH, Hamburg (DE)

(72) Inventor: Jelle Dijkstra, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 861 days.

(21) Appl. No.: 16/979,773

(22) PCT Filed: Mar. 12, 2019

(86) PCT No.: PCT/EP2019/056172
§ 371 (c)(1),
(2) Date: Sep. 10, 2020

(87) PCT Pub. No.: WO2019/175181
PCT Pub. Date: Sep. 19, 2019

(65) Prior Publication Data
US 2021/0015539 A1   Jan. 21, 2021

(30) Foreign Application Priority Data

Mar. 13, 2018   (DE) .......................... 102018105812.8

(51) Int. Cl.
*A61B 18/12* (2006.01)
*A61B 18/00* (2006.01)

(52) U.S. Cl.
CPC   *A61B 18/1206* (2013.01); *A61B 2018/00702* (2013.01); *A61B 2018/1213* (2013.01)

(58) Field of Classification Search
CPC ...... A61B 18/1206; A61B 2018/00702; A61B 2018/1213
See application file for complete search history.

(56) References Cited

U.S. PATENT DOCUMENTS 6,210,403 B1 * 4/2001 Klicek ............... A61B 18/1206
606/34
6,730,080 B2   5/2004 Harano et al.
(Continued)

FOREIGN PATENT DOCUMENTS

CN   101027007 A   8/2007
CN   101883534 A   11/2010
(Continued)

OTHER PUBLICATIONS

Feb. 7, 2023 Office Action issued in Chinese Patent Application No. 201980018360.5.
(Continued)

*Primary Examiner* — Sean W Collins
(74) *Attorney, Agent, or Firm* — Oliff PLC

(57) ABSTRACT

A high-frequency generator connects an electrosurgical instrument, including an electrical output connection point for an electrosurgical instrument, a power supply, which is at least indirectly connected to the output connection point, and a power controller for controlling the electrical output power output via the output connection point. The power controller is designed to begin the output of an electrical output power when an output energy balance amount is greater than an output energy limit value and to end the output of the electrical output power when the output energy balance amount falls below a minimum value.

9 Claims, 4 Drawing Sheets

(56) References Cited

U.S. PATENT DOCUMENTS

Figure 1:
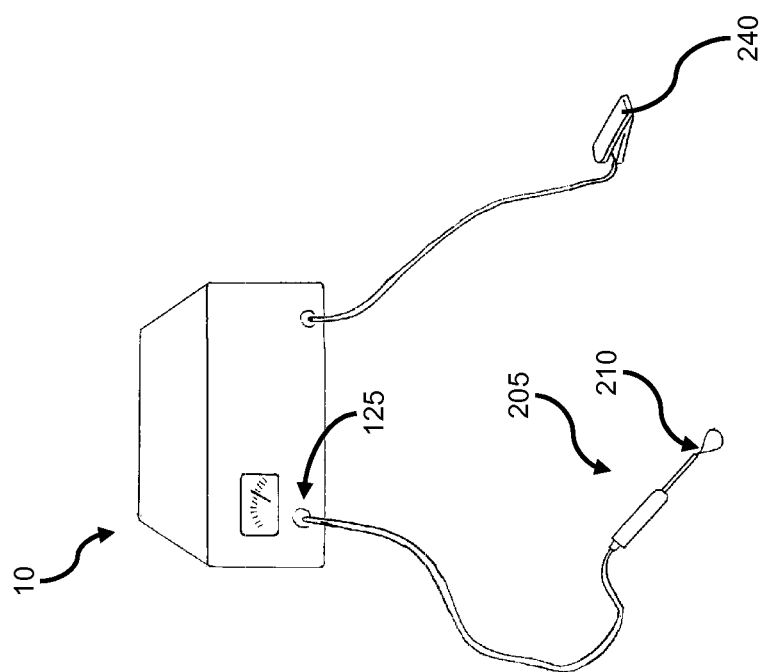

| | | | |
|---|---|---|---|
| 2002/0052599 A1* | 5/2002 | Goble | A61B 18/1445 606/51 |
| 2004/0138654 A1 | 7/2004 | Goble | |
| 2009/0275938 A1 | 11/2009 | Roggan et al. | |
| 2012/0123400 A1* | 5/2012 | Francischelli | A61B 18/12 606/41 |

FOREIGN PATENT DOCUMENTS

| | | |
|---|---|---|
| WO | 95/09577 A1 | 4/1995 |
| WO | 02/011634 A1 | 2/2002 |
| WO | 2004/062516 A1 | 7/2004 |
| WO | 2010/108523 A1 | 9/2010 |

OTHER PUBLICATIONS

Jun. 3, 2019 Search Report issued in International Patent Application No. PCT/EP2019/056172.
Jun. 3, 2019 Written Opinion of the International Searching Authority issued in International Patent Application No. PCT/EP2019/056172.

\* cited by examiner

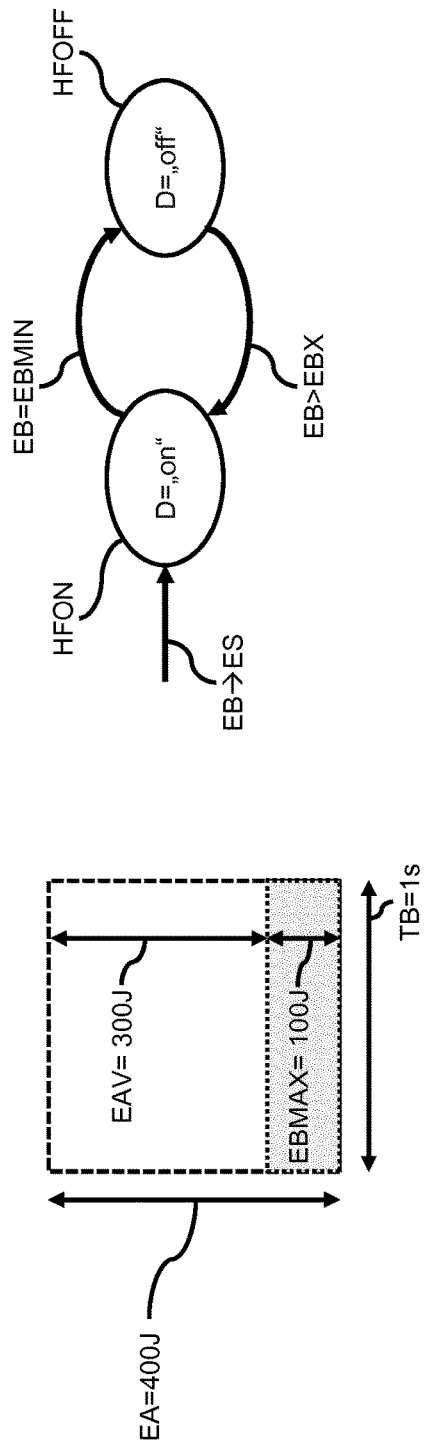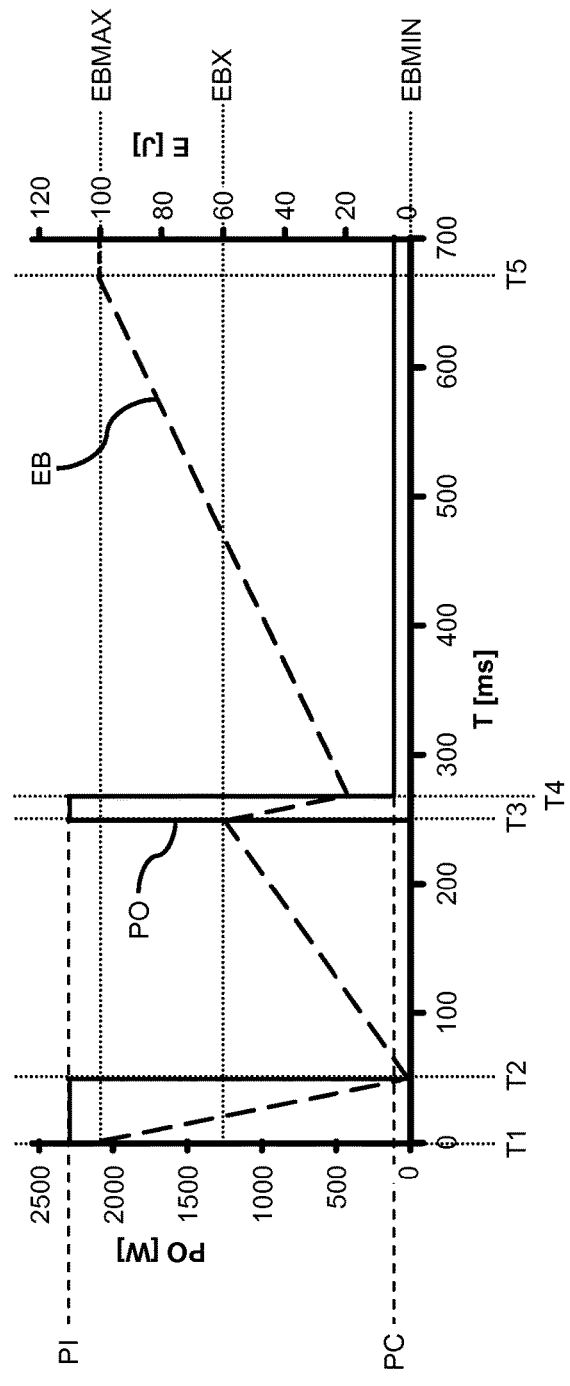
Fig. 3A
Fig. 3B
Fig. 3C

HIGH-FREQUENCY GENERATOR, CONTROL UNIT, METHOD FOR OPERATING A HIGH-FREQUENCY GENERATOR

The invention relates to a high-frequency generator for connecting an electrosurgical instrument, comprising an electrical output connection point for an electrosurgical instrument, a power supply, which is at least indirectly connected to the output connection point, and a power controller for controlling the electrical power output via the output connection point.

High-frequency generators, in particular high-frequency generators for supplying electrosurgical instruments, are generally known. The creation of a cutting plasma for cutting body tissue requires a high ignition power, which is usually multiple times greater than a permissible average power of a generator. For this reason, it makes sense to pulse the electrical output power of a generator, i.e. to deliver it in pulses. Appropriately long pauses between the pulses make it possible to ensure that a permissible average power of the generator is not exceeded despite the high ignition power.

WO 2010/108523 describes a high-frequency generator for the connection of an electrosurgical instrument for cutting body tissue by means of an arc. The instrument comprises a power control for controlling the electrical power delivered by way of the output terminal. The power control is adapted firstly to cause delivery of a high output power for a phase for the initial cutting support and subsequently thereto either if ignition of an arc has occurred during the phase for initial cutting support for a predetermined period of time of a cutting phase to cause the delivery of a power which is reduced in relation to the high power and subsequently for a predetermined period of time of a long pause interval to cause the delivery of no power or a lower power at which no arc occurs, or if no ignition of an arc has occurred until the attainment of a predetermined maximum duration of the phase for initial cutting support to cause the delivery of no power or a lower power for a predetermined period of time of a short pause interval.

The invention is based on the object of defining an improved high-frequency generator that provides an as consistently good power control as possible under different environmental conditions.

To this end, the invention proposes a high-frequency generator according to claim 1.

The high-frequency generator is configured to connect an electrosurgical instrument and comprises an electrical output connection point for an electrosurgical instrument, a power supply, which is at least indirectly connected to the output connection point, and a power controller for controlling the electrical output power output via the output connection point.

The power controller is configured to begin the output of an electrical output power when an output energy balance amount is greater than an output energy limit value, wherein the output energy balance amount is determined over a moving determination duration from a supplied specified generator power and the output electrical output power.

The invention is based on the consideration that—especially in light of the aforementioned approach used in prior art—the determination of a suitable electrical output power can still be improved. The term "determining" the output energy balance amount means that a value is formed that represents the actual balance of a specified generator power and the output electrical output power as accurately as possible, however at least sufficiently accurately for control purposes. The term "specified generator power" means a power that can be adjusted by the user which is to be output by the generator via the electrode and is averaged over the determination duration.

A first aspect relates to the determination of suitable pulse durations and the durations of the pauses in between. Especially the approach mentioned at the beginning, where the pulse duration and/or pause duration are set as fixed windows of time, can lead to the case where, after the end of the pulse duration, the delivery of an energy pulse is ended despite the fact that a plasma is currently being successfully generated.

Likewise, the approach known from prior art may lead to the case that the user tends to choose too long pause durations in order to ensure that a maximum permissible energy amount dictated by law and/or standards is not exceeded during a balance duration, or to the case that pauses occur more frequently than necessary. This means that potentially available energy reserves are not used.

The invention includes the finding that flexible control of the electrical output power that is, in particular, adapted to the ambient conditions, allows for a better use of existing energy reserves without a maximum permissible generator power being exceeded. It makes it, in particular, possible to control pulses with an ignition power for igniting a plasma in such a way that they last longer, as long as an energy amount resulting from a maximum permissible generator power is not exceeded—this is, in particular, an advantage over a fixed pulse duration.

Another aspect relates to the ability to better control the output energy. A purely time-based control of the output energy—as disclosed in the prior art mentioned at the beginning—entails the risk of uncontrolled, repeated switching between an ignition power and a cutting power, which may occur especially in case of unstable cutting plasma or if the value specified for the generator power is too low. In this case, the repeated delivery of the high ignition power can lead to an uncontrollably high energy input into the tissue.

An output energy balance amount within the meaning of a virtual energy storage unit, where an emptying of the storage unit is taken into consideration, makes it possible to determine by means of an actual output energy amount how much energy has already been used in a previous, moving determination duration, and, subsequently, how much energy is currently still available based on the specified regulations. Thus, the risk of an uncontrollably high energy input into the tissue to be treated can be reduced or even minimized in an advantageous manner without the specification of a fixed time limit for the energy output.

In this context, "moving" means that, as a balance frame, the determination duration has a fixed duration, but moves as the time passes, which leads to the creation of a rolling time window, in which the output energy balance amount is re-calculated iteratively, for example in each new program cycle or per specified cycle duration. A specified generator power and an—actually output—output energy balance amount, in particular, are taken into account for the calculation. This means that, figuratively speaking, a virtual energy storage unit defined by a determination duration and a maximum output energy balance amount is supplied energy in accordance with a specified generator power, while energy is also taken out of said storage unit in accordance with an electrical output power. The specified generator power determines how much energy is supplied to the virtual energy storage unit, while, at the same time, the actually output electrical ouput power is taken out of it. The resulting difference is the output energy balance amount.

Preferably, it is provided that the specified generator power is adjustable. Specifically, this includes the option of adjusting the value of the specified generator power, in particular a scalar numerical value with the unit watts, via a suitable user interface or a control element. Such a control element may, for example, be configured as a rotary control element or as an arrangement of arrow keys, and may comprise a display that shows the currently set value of the specified generator power. The adjustability of the specified generator power makes it possible to advantageously influence the output of electrical output energy and to thus adapt it to specific applications. In this regard, statutory and/or normative requirements might have to be taken into consideration, in particular as a maximum power limit.

Preferably, it is provided that the output energy balance amount does not exceed a maximum output energy balance amount. Specifically, this means that the output energy balance amount is limited and that—figuratively speaking—the virtual energy storage unit has a maximum capacity beyond which no additional energy will be stored. A maximum output energy balance amount can ensure that statutory and/or normative requirements are complied with, especially in consideration of the specified generator power. These requirements concern in particular a maximum permissible energy amount to be output within a determination period. Such a framework is, in particular, specified in the DIN EN 60601-2-2 guideline, entitled "Medical electrical equipment—Part 2-2: Particular requirements for the basic safety high frequency surgical equipment", which describes that a maximum permissible energy amount of 400 J is not exceeded within a determination period of one second. In such an embodiment, the risk of exceeding a maximum energy amount can be advantageously reduced, in particular in order to guarantee patient safety. In a possible embodiment, the maximum output energy balance amount can be set to a value that is a certain amount, for example ten percent, smaller than the maximum output energy balance amount, in order to provide a safety buffer, for example so as to further reduce the risk of exceeding statutory and/or normative requirements.

As part of one embodiment, it is provided that the maximum output energy balance amount is determined from the difference of a permissible energy amount and an output energy amount, whereby the permissible energy amount is the maximum energy amount that may be output during a balance duration. Requirements regarding the permissible energy amount and the balance duration may arise due to statutory and/or normative provisions. In this regard, the embodiment—in connection with an output energy balance amount—makes it possible to achieve compliance with statutory and/or normative requirements, while, at the same time, the maximum available output power is—within said requirements—used at all times. This aspect must, in particular, be seen in contrast to prior art, where compliance with such requirements is achieved in particular through specified, conservatively configured pause durations between output energy pulses—ignition pulses in particular—which means that potentially available power cannot be used. In preferred embodiments, the balance duration may be equal to the determination duration.

The output energy limit value may be adjustable. The adjustability of the output energy limit value makes it possible to advantageously influence the behavior of the power controller—and thus the cutting behavior of the high-frequency generator. A low output energy limit value means that, after a point in time at which the output energy balance amount is zero—i.e. at which the energy storage unit has been emptied completely—it will take less time for an energy amount required for the output of the output power—of an ignition power, in particular—to be once again available to the high-frequency generator. However, a small output energy limit value also means that it will take less time until the output energy balance amount once again drops under the minimum amount, in particular to zero. It is also true that the energy available in the storage unit will not be sufficient for igniting a plasma if the chosen output energy limit value is too low. However, if a greater output energy limit value is chosen, more output energy—in particular for longer ignition pulses—will be available once the output energy limit value has been reached. However, in this case, the pause durations, i.e. the waiting time until the output energy limit value is reached, will be correspondingly longer as well.

In the context of one embodiment, it is provided that the power controller has a balancing unit that is configured to cyclically determine the output energy balance amount. Specifically, this means that the balancing unit always updates the virtual energy storage unit by cyclically recalculating the balance amount. The cyclic recalculation takes place within a cycle time that is shorter than the determination duration. In possible embodiments, the cycle time is shorter than the determination duration at least by the factor 100, preferably by the factor 1,000 and particularly preferably by the factor 10,000. In case of a determination duration of 1 second, for example, a value between 100 μs and 5 ms may be chosen for the cycle time. A short cycle time means that a current value of the output energy balance amount is available to the power controller at all times so that the electrical output power can be controlled on the basis of the output energy balance amount subject to a negligible delay.

In order to achieve the object mentioned at the beginning, furthermore, a power controller for a high-frequency generator is proposed. The high-frequency generator comprises an electrical output connection point for an electrosurgical instrument, a current or voltage source, which is at least indirectly connected to the output connection point, and a power controller. The power controller is configured to begin the output of an electrical output power when an output energy balance amount is greater than an output energy limit value or has an initial value, and to end the output of the electrical output power when the output energy balance amount falls below a minimum value, wherein the output energy balance amount is determined over a moving determination duration, wherein the output energy balance amount is formed as a difference from a specified generator power and the electrical output power. The power controller according to the invention uses the advantages of the high-frequency generator according to the invention in an advantageous manner. In possible embodiments of the power controller, it can be configured such that it is suitable for upgrading existing high-frequency generators. To this end, the power controller may be configured as a—in particular replaceable—hard- and/or software module.

In order to achieve the object mentioned at the beginning, furthermore, a method of operating a high-frequency generator is proposed. The method comprises the following steps:

initializing an output energy balance amount to an initial energy; and selectively beginning an output of an electrical output power, in particular through the operation of a foot switch, when an output energy balance amount is greater than an output energy limit value or has an initial energy.

In one embodiment of the method, it is provided that the output of the electrical output power is ended when the output energy balance amount is zero.

In another embodiment of the method, it is provided that the output energy balance amount is determined over a moving determination duration from a supplied specified generator power and the output electrical output power.

The method for operating a high-frequency generator according to the invention uses the advantages of the high-frequency generator in an advantageous manner.

Figure 2:
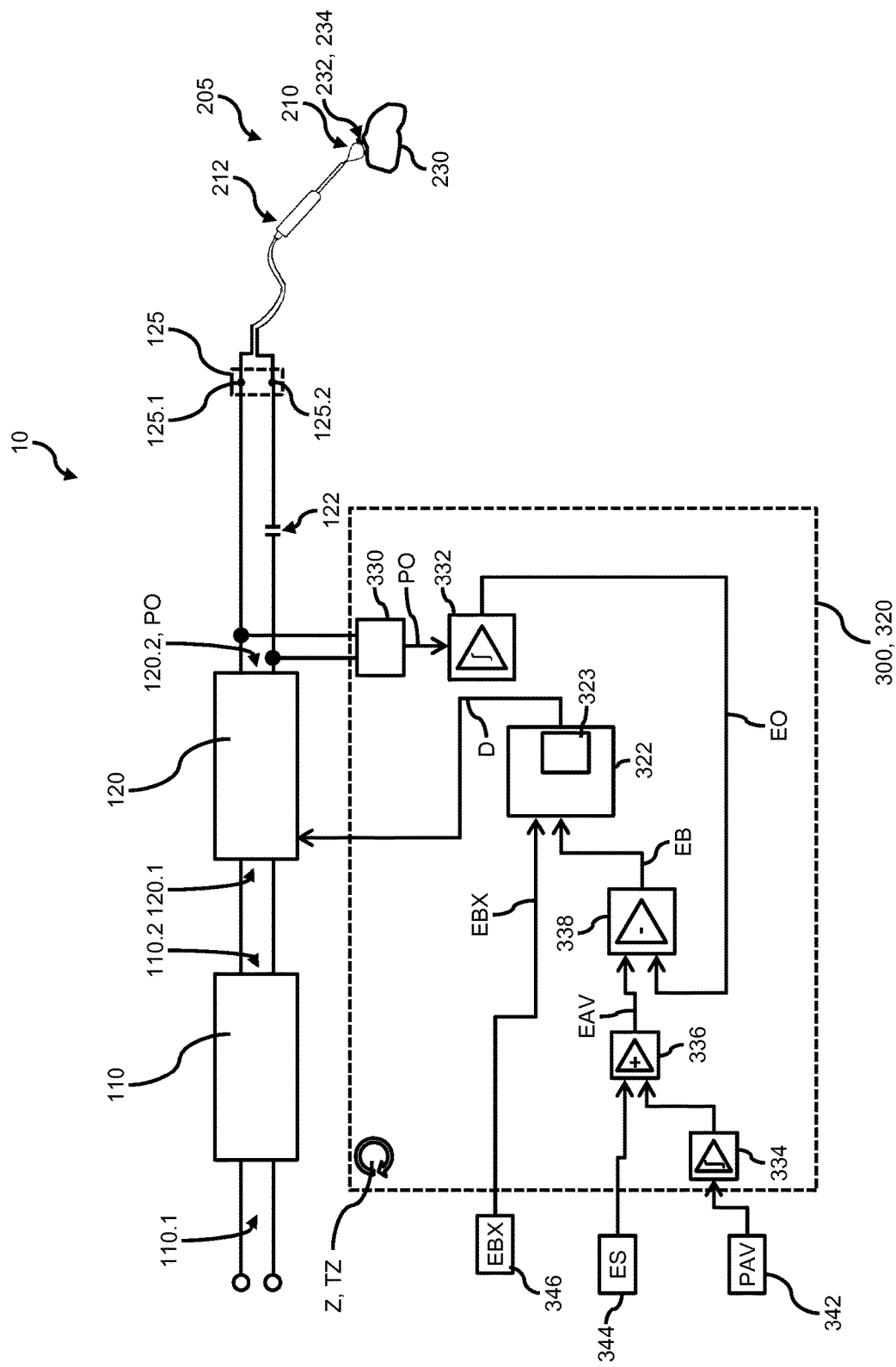
Figures 4A, 4B:
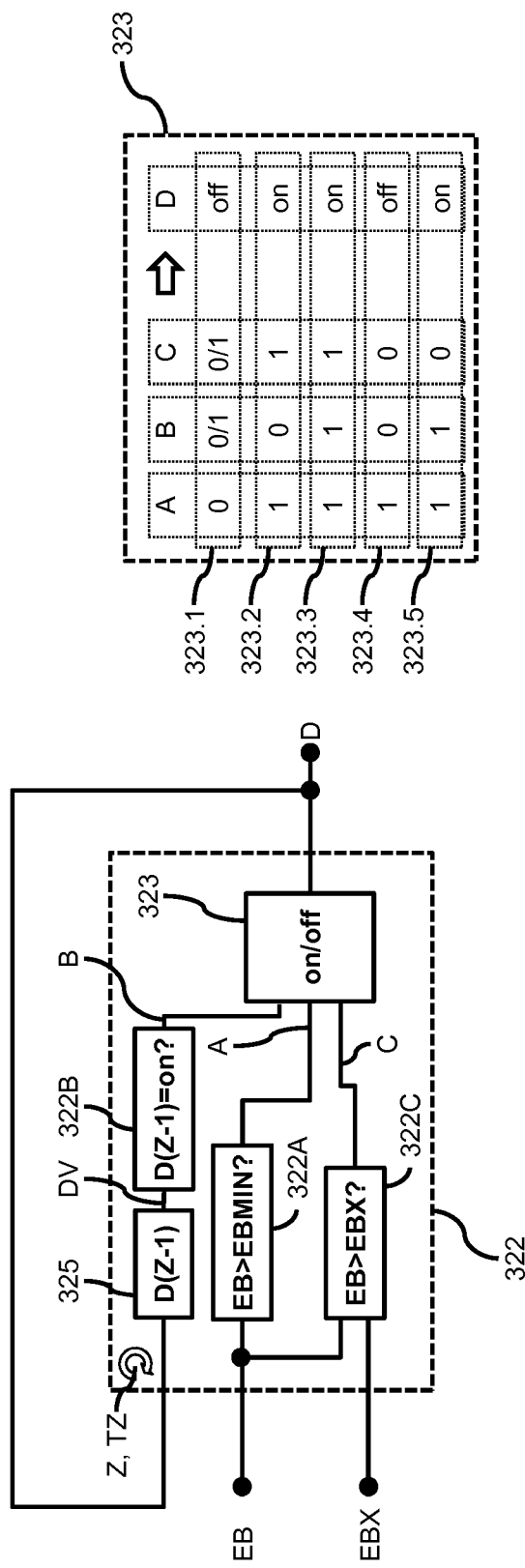

Further advantages, features and details of the invention can be inferred from the following description of the preferred embodiments and from the drawings. The drawings show the following:

FIG. 1: a high-frequency generator with a connected electrosurgical instrument;

FIG. 2: a schematic diagram of a high-frequency generator according to the concept of the invention;

FIG. 3A: a schematic illustration of the determination of a maximum output energy balance amount;

FIG. 3B: a state diagram for a possible operation of the high-frequency generator;

FIG. 3C: a flow diagram with schematic curves of the output power and the output energy balance amount;

FIG. 4A, B: a detailed schematic diagram of an activator and possible switching states of a switch-on module.

FIG. 1 shows a high-frequency generator 10 that, on the input side, is provided with a power cable for connecting it to a power supply system. The high-frequency generator 10 is connected to a foot switch 240 for activating the high-frequency generator 10. On the output side, two output connection terminals—which are not shown in detail—namely, a first output terminal 125.1 and a second output terminal 125.2, of an output connection point 125 of the high-frequency generator 10 are connected to a bipolar electrode 210 of an electrosurgical instrument 205 via power lines. The electrosurgical instrument has a bipolar cutting electrode 210 that, in the exemplary embodiment according to FIG. 1, is configured as a bipolar loop cutting instrument.

FIG. 2 shows the schematic diagram of a preferred embodiment of the high-frequency generator 10 according to the invention which, compared to prior art, has an improved initial cutting behavior. The shown exemplary embodiment is suitable for surgical interventions in particular in the area of transurethral resection (TURis), but also in other areas such as endoscopic mucosal resection (EMR) and polypectomy.

The high-frequency generator 10 comprises a power supply 110, that can be connected to an AC supply network at an input 110.1 and is, on the output side, at an output 110.2, connected to an input 120.1 of a clock-controllable high-frequency generator module 120. The power supply 110 converts an AC voltage into a DC voltage.

The high-frequency generator module 120 converts the DC voltage into an AC voltage with a frequency between 0.3 and 2 MHz. An output 120.2 of the high-frequency generator module 120 is connected to a bipolar electrode 210 of an electrosurgical instrument 205 via at least one anti-faradization capacitor 122 and via a bipolar electrical output connection point 125 of the high-frequency generator. The at least one antifaradization-capacitor is to prevent the transmission of direct currents. The AC voltage is output at the output 120.2 in a clock-controlled manner. "Clock-controlled" means that by means of an activator 322 the high-frequency generator module 120 can be clocked in such a way that pulse sequences with pulses of different pulse lengths and different pulse profiles are made available at the output 120.2. The pulse amplitude my change over the course of the pulse. The power output of the high-frequency generator module 120 is time-controlled in such a way that, depending on an output energy balance amount EB, a sequence of an electrical output power of different power levels and durations can be output.

The electrosurgical instrument 205 will usually consist of a cutting electrode 210 and a handle part 212. To make it possible to electrosurgically cut a tissue 230—which is shown in part in the figure—in the vicinity of the cutting electrode 210, a saline solution 232 can be applied to the area of the body tissue 230 which is to be operated on, and a plasma 234 can be generated in this area by the electrode 210. This is achieved through the output of a high-frequency current with high electrical power, in particular an ignition power PI, at the output 120.2 of the high-frequency generator module 120. The bipolar cutting electrode 210 of the electrosurgical instrument is connected to the output 120.2 of the high-frequency generator module 120 via the bipolar electrical output connection point 125. The high-frequency current output by the bipolar cutting electrode 210 heats the saline solution 232 in the area of the bipolar cutting electrode 210, so that the plasma 234 is ignited. The plasma 234 enables the surgeon to make a desired incision in the tissue 230 adjacent to the cutting electrode 210. The surgeon can generally start and end the cutting process by using a foot switch 240 (not shown).

A comparatively smaller electrical power, in particular a cutting power PC, is sufficient for maintaining the plasma required for electrosurgical cutting. This is the case, because the plasma has a significantly higher electrical resistance than the saline. The electrical resistance of the plasma can be in the range of several hundred ohms, while the electrical resistance of the saline can, for example, be in the range of approx. 25 ohms.

The high-frequency generator 10 comprises a power controller 300, which, in turn, comprises a balancing unit 320.

The balancing unit 320 comprises a power measuring unit 330. The power measuring unit 330 is connected to the output 120.2 of the high-frequency generator module 120 in such a way that an actually output electrical output power PO can be detected, and, in particular, be measured. The output of the power measuring unit 330 is connected to a first integrator 332. The first integrator is configured to integrate the value, in particular the measured value, of the electrical output power PO over a determination duration TA, in order to determine the output energy amount EO actually output by the high-frequency module 120 during this determination duration TA.

The balancing unit 320 further comprises a second integrator 334. Said second integrator 334 is configured to integrate a value for a specified generator power PAV over the detremination duration TA. On the input side, the second integrator 334 is connected to a generator power adjustment module 342, by means of which a specified generator power PAV can be adjusted by the user. On the output side, the second integrator 334 transmits the result of the integration to an adder 336 that adds an initial energy ES to the integral of the specified generator power and thus determines a specified energy amount EAV. In certain embodiments, the specified energy amount EAV can alternatively be formed in a simplified manner, in which the specified generator power PAV is multiplied by the determination duration TA. In this case, the following applies: EAV=PAV*TA.

The initial energy ES to be added to the integral of the specified generator power by the summator 336 can be set via an initial energy adjustment module 344. The initial energy ES must, in particular, be chosen in such a way that a maximum output energy balance amount EBMAX is not exceeded.

In a subtractor 338, the output energy amount EO is subtracted from the specified energy amount EAV in order to form the output energy balance amount EB. This leads to the following formulaic relationship:

$$EB = ES + \int_{TA} PAV - \int_{TA} PO = EAV - EO$$

On the input side, an activator 322 is connected to the subtractor 338 and to a limit value adjustment module 346. An output energy limit value EBX can be adjusted via the limit value adjustment module 346. The output energy limit value EBX defines in particular the minimum amount of an increasing output energy balance amount EB, wherein, once said minimum amount is reached, an electrical output power PO, in particular an ignition power PI, is output. This means that an ignition power will only be output if more than a minimum energy amount defined by the output energy limit value EBX is available in the virtual energy storage unit. Depending on the incoming values, namely the output energy balance amount EB and the output energy limit value EBX, the activator 322 outputs a switch-on signal D. In order to be able to transmit the switch-on signal D to the high-frequency generator module 120, the activator 322 is, on the output side, connected to the high-frequency generator module 120 in a signal-carrying manner. Via the switch-on signal D, the output of an output energy PO by the high-frequency generator module 120 can be activated and deactivated, i.e. begun and ended.

The balancing unit 320 works with a cycle time TZ, which means that, after a cycle T with a cycle time TZ, the calculations for forming the output energy balance amount EB described above will be once again performed in a new cycle T+1 with updated input data, in particular with the current specified generator power PAV and the current output power PO. Thus, the values for the output energy amount EO and the specified energy amount EAV are updated in each cycle T. The cycle time TZ may, in particular, depend on the specific configuration of the balancing unit, especially on the hard- and software used, and may, for example, be between 100 μs and 5 ms.

The power controller 300 may also be realized, in full or in parts, in a microcontroller, in which the component 320 and optional further components are programmed.

FIG. 3A schematically shows a diagram for determining a maximum output energy balance amount EBMAX and therefore—in the figurative sense—for determining the size of the energy storage unit. The outer frame, represented by the dashed line in the figure, is formed by technical and/or legal and/or normative requirements. Such a frame may consist in the requirements of DIN EN 60601-2-2, entitled "Medical electrical equipment—Part 2-2: Particular requirements for the basic safety high frequency surgical equipment", which specifies that a permissible energy amount EA of 400 J must not be exceeded within a balancing duration TB. Within a balancing duration TB of one second, an adjustable, specified generator power PAV, for which in this case PAV=300W has been chosen by way of example, leads accordingly to the output of a specified energy amount EAV of 300 J. The maximum output energy total amount EBMAX, which, in the present case is 100 J, results from the difference between the permissible energy amount EA and the specified energy amount EAV.

FIG. 3B shows a state diagram for a possible operation of the high-frequency generator. After the activation and/or initialization of the output energy balance amount EB with an initial energy ES, the high-frequency generator 10 is in an activated state HFON. In this activated state HFON, the switch-on signal D has the value "on"; consequently, the high-frequency generator module 120 outputs an electrical output power PO. If the output energy balance amount EB is below a minimum value EBMIN, and is, for example, zero—i.e. if the virtual energy storage unit is completely emptied—the high-frequency generator 10 will switch into a deactivated state HFOFF. In the deactivated state HFOFF, the switch-on signal D has the value "off"; consequently, the high-frequency generator module 120 does not output an electrical output power PO. In this deactivated state HFOFF, the output energy balance amount EB once again increases, especially due to the supply of the specified generator power PAV; this means that the virtual energy storage unit is recharged. As soon as the output energy balance amount EB has exceeded an output energy limit value EBX, the high-frequency generator 10 will switch once again into the activated state HFON. A high initial energy ES, that may at most have the value of the maximum output energy balance amount EBMAX, leads to the longest possible output duration after activation. In the context of the invention, it can be generally advantageous to choose the same value as for the output energy limit value EBX as the value for the initial energy ES. In that case, the first ignition attempt after the initialization corresponds, in particular with regard to the pulse duration and the subsequent waiting duration, to the subsequent ignition attempts respectively taking place after the output energy limit value EBX has been reached. It may be provided that the initial energy ES is only introduced once, at the beginning of the treatment.

FIG. 3C shows a diagram of the development of an electrical output power PO and of an output energy balance amount EB of an embodiment of a high-frequency generator 10 pursuant to the concept of the invention over time. At a first point in time T1, the electrical output energy PO has the value of an ignition power PI, which, in the present case, is 2,300 W. In the present case, an adjustable specified generator power PAV is 300 W and the maximum output energy balance amount EBMAX is—as shown in FIG. 3A—100J.

The output energy balance amount EB can be used to ensure that—within a determination duration TA—a certain output energy amount, namely a maximum output energy balance amount EBMAX is not exceeded. In this context, the output power PO may for a short period of time, especially during a period of time within the determination duration TA, be greater than an average output power resulting from the quotient of said maximum output energy balance amount EBMAX and the determination duration TA. However, a greater output power PO means that the output energy balance amount EB decreases faster than new energy can be added in accordance with the maximum virtual output power. In other words—in the sense of a virtual energy storage unit—the output energy balance amount EB is discharged faster than it is charged.

At a point in time T2, the output energy balance amount EB is equal to the minimum output energy balance amount EBMIN, i.e. the virtual energy storage unit is depleted. In that case, the output energy balance amount EBMIN is zero. Thus, the pulse duration of the ignition pulse that started at point in time T1 ends at point in time T2. Since the specified generator power PAV is 300 W and the ignition power PI is 2,300 W, the power difference is 2,000 W. At a maximum output energy balance amount EBMAX of 100 J (and an initial initial energy ES of 100 J), point in time T2 is reached after 0.05 s, i.e. 50 ms. At point in time T2, the output of an electrical output energy PO by a high-frequency generator module 120 is ended, i.e. the high-frequency generator 10 is switched into the deactivated state HFOFF. Consequently, in the diagram, the value PO falls gradually from the ignition power PI to zero. As of point in time T2, the output energy balance amount EB begins to increase, namely at a rate that corresponds to the specified generator power PAV=300 W=300 J/s. At a third point in time T3, the output energy balance amount EB has reached the output energy limit value EBX, which, in the present case, is 60 J. Consequently, the third point in time T3 occurs 0.2 s=200 ms after the second point in time T2 and T3=250 ms. The period of time between the point in time T2 and the point in time T3 is a waiting duration, during which no electrical output energy PO is output.

As of point in time T3, i.e. once the output energy limit value EBX has been reached, the high-frequency generator module 120 is controlled via a switch-on module 323 in such a way that an electrical output power PO is output. Due to the low output resistance at the bipolar electrode, the electrical output power PO takes on a relatively high value, namely in the amount of the ignition power PI. At a point in time T4 a plasma was successfully ignited, whereupon the output resistance at the bipolar electrode increases, and, consequently, the output power PO abruptly drops to a lower value, in particular to a cutting power PC, wherein the cutting power PC is multiple times smaller than the ignition power PI. In the present case, the cutting power PC is 100 W.

Due to the fact that the cutting power PC that is now output is smaller than the specified generator power PAV, the output energy balance amount EB starts to increase at the fourth point in time T4. Figuratively speaking, this means that the virtual energy storage unit is charged faster than it is emptied. As a result, at a fifth point in time T5, the output energy balance amount EB has reached its maximum value, namely the maximum output energy balance amount EBMAX, that, in the present case, is 100 J. At a cutting power PC of 100 W and a specified generator power PAV of 300 W, the power difference is 200 W=200 J/s.

The cutting process with an electrosurgical instrument 205 can be continued beyond point in time T5, either until the cutting process is terminated through the release of the foot switch 240, or until the plasma is interrupted. At this point in time, which is not shown in the figure, an initial cutting approach as described herein can be repeated.

FIG. 4A shows a schematic diagram of a potential configuration of an activator 322. In the present case, the activator 322 has three comparison modules 322A-C as well as a cycle memory 325 and a switch-on module 323. In the present case, the way in which the activator 322 works during a cycle Z is illustrated.

In a first comparison module 322A, it is checked whether the value of the output energy balance amount EB is greater than the minimum output energy balance amount EBMIN, in particular greater than zero. If this is the case, a first comparison signal A is output and transmitted to the switch-on module 323. This comparison signal A, and also the comparison signal of the other comparison modules 322B, 322C, can, in particular, be of a Boolean nature, i.e. exclusively have either the value zero or one.

A cycle memory 325 stores a switch-on signal D output by the switch-on module 323 in the previous cycle Z−1 and provides said signal in the current cycle Z as the previous switch-on signal DV on the output side. A second comparison module 322B, that is connected to the cycle memory 325, checks whether the previous switch-on signal DV is positive, i.e. DV=D(Z−1)="on". If this is the case, a positive second comparison signal B is output and transmitted to the switch-on module 323.

A third comparison module 322C compares the output energy balance amount EB with the output energy limit value EBX. If the output energy balance amount EB is greater than the output energy limit value EBX, figuratively speaking, the energy storage unit is filled to a specified minimum value. In this case, a positive third comparison signal C is output and transmitted to the switch-on module 323.

Depending on the comparison signals A, B, C, the switch-on module 323 outputs a switch-on signal D, which can have the value "on" or "off". Nevertheless, as an alternative or in addition to the switch-on module 323, the switch-on signal may be output in Boolean form, i.e. accordingly as 1 for "on" and 0 for "off".

FIG. 4B shows possible switching states 323.1-5 of a switch-on module 323. In a first switching state 323.1, the first comparison signal A is negative, i.e. A=0. Regardless of whether the second comparison signal B or the third comparison signal C are positive or negative, this means a negative switch-on signal D. A negative switch-on signal D, i.e. the switching position "off", has the result that no electrical output power PO is output by the high-frequency generator module 120. This switching state 323.1 means that the output energy balance amount EB at the current point in time is equal to zero and that, figuratively speaking, the virtual energy storage is empty.

In a second switching state 323.2, the first comparison signal A and the third comparison signal C are positive, and the second comparison signal B is negative, which leads to a positive switch-on signal D, i.e. the switching position "on". This switching state 323.2 occurs if the output energy balance amount EB in the current cycle Z is greater than the output energy limit value EBX, and if, in the previous cycle Z−1, the switch-on module 323 output a negative switch-on signal D, so that consequently the high-frequency generator module 120 did not output any output power PO in the previous cycle Z−1.

In a third switching state 323.3, all three comparison signals A, B, C are positive, which leads to a positive switch-on signal D, i.e. the switching position "on". This switching position 323.3 means that the output energy balance amount EB at the current point in time is greater than the output energy limit value EBX and that the switching module 323 output a positive switch-on signal D in the previous cycle. The latter means that the high-frequency generator module 120 output an output power PO in the previous cycle Z−1.

In a fourth switching state 323.4, the first comparison signal A is positive, and the second comparison signal B and the third comparison signal C are negative, which leads to a negative switch-on signal D, i.e. the switching position "off". This switching state 323.4 means that the output energy balance amount EB at the current point in time is smaller than the output energy limit value EBX, and that, in the previous cycle Z−1, the switch-on module 323 output a negative switch-on signal D, i.e. that the high-frequency generator module 120 did not output any output power PO.

In a fifth switching state 323.5, the first comparison signal A and the second comparison signal B are positive, and the third comparison signal C is negative, which leads to a positive switch-on signal D, i.e. the switching position "on". This switching state 323.5 means that the output energy balance amount EB at the current point in time is decreasing and smaller than the output energy limit value EBX, and that, in the previous cycle Z−1, the switch-on module 323 output a positive switch-on signal D, i.e. that the high-frequency generator module 120 output an output power PO.

In connection with the switching states, especially the fourth switching state 323.4 and the fifth switching state 323.5 need to be mentioned: in both switching states 323.4, 323.5, the output energy balance amount EB is smaller than the output energy limit value EBX.

In the fourth switching state 323.4, the previous switch-on signal DV, i.e. the switch-on signal D in a previous cycle Z−1, was negative, i.e. no output energy PO was output by the high-frequency generator module 120.

However, if—as in case of the fifth switching state 323.5—the switch-on signal D was positive in a previous cycle Z−1, i.e. if the high-frequency generator module 120 output an output energy PO, the high-frequency generator module 120 will continue to output an output energy PO, due to the output of a positive switch-on signal D by the switch-on module 323 in a current cycle Z. In simple terms: an activated high-frequency generator module 120 will remain activated—even if the output energy balance amount EB falls below the output energy limit value EBX—and will only be deactivated if the output energy balance amount EB falls below the minimum output energy balance amount EBMIN, in particular, if it is equal to zero. "Activated" and "deactivated" refer in particular to the output of an electrical output energy PO via the output 120.2 of the high-frequency generator module 120 and do not mean that the power supply 110 and/or the high-frequency generator 10 in its entirety is switched on and/or off.

LIST OF REFERENCE NUMBERS

- 10 high-frequency generator
- 110 power supply, clocked power supply
- 110.1 power supply input
- 110.2 power supply output
- 120 high-frequency generator module
- 122 antifaradization capacitor
- 125 output connection point, output poles of the high-frequency generator
- 125.1 first output terminal
- 125.2 second output terminal
- 205 electrosurgical instrument
- 210 cutting electrode, bipolar electrode of the electrosurgical instrument
- 212 handle part of the electrosurgical instrument
- 230 tissue
- 232 saline solution, saline
- 234 plasma
- 240 foot switch
- 300 power controller
- 320 balancing unit
- 322 activator
- 322A first comparison module
- 322B second comparison module
- 322C third comparison module
- 323 switch-on module
- 323.1-5 first to fifth switching state
- 325 cycle memory
- 330 power detection unit
- 332 first integrator
- 334 second integrator
- 336 adder
- 338 subtractor
- 342 generator power adjustment module
- 344 initial energy adjustment module
- 346 limit value adjustment module
- 348 multiplier
- 356 ignition voltage
- 610 virtual energy storage
- 630 actual energy amount
- A, B, C first to third comparison signal
- D switch-on signal
- DV previous switch-on signal
- EA permissible energy amount
- EAV output energy amount
- EB output energy balance amount
- EBMAX maximum output energy balance amount
- EBMIN minimum output energy balance amount, minimum value
- EBX output energy limit value
- EO output energy amount
- ES initial energy
- HFOFF deactivated state of the high-frequency generator
- HFON activated state of the high-frequency generator
- PAV specified generator power
- PC cutting power
- PI ignition power
- PO output power, electrical power
- T time
- TA determination duration
- TB balance duration
- TI point in time of ignition
- TZ cycle time
- Z cycle, calculation cycle

The invention claimed is:

1. A high-frequency generator for connecting an electrosurgical instrument, comprising
   an electrical output connection point for an electrosurgical instrument,
   a power supply, which is at least indirectly connected to the output connection point,
   a power controller for controlling an electrical output power output via the output connection point,
   wherein
   the power controller is configured
   to begin the output of the electrical output power when an output energy balance amount is greater than an output energy limit value and
   to end the output of the electrical output power when the output energy balance amount falls below a minimum value,
   the output energy balance amount being determined over a moving determination duration from a supplied specified generator power and the output electrical output power.

2. The high-frequency generator according to claim 1, wherein the specified generator power is adjustable.

3. The high-frequency generator according to claim 1, wherein the output energy balance amount does not exceed a maximum output energy balance amount.

4. The high-frequency generator according to claim 1, wherein a maximum output energy balance amount is determined from a difference between a permissible energy amount and a specified energy amount, wherein the permissible energy amount is a maximum energy amount that may be output during a balance duration, and the specified energy amount is determined from the specified generator power during the balance duration.

5. The high-frequency generator according to claim 1, wherein the output energy limit value is adjustable.

6. The high-frequency generator according to claim 1, wherein the power controller comprises a balancing unit, which is configured to cyclically determine the output energy balance amount.

7. A method for operating a high-frequency generator according to claim 1, which comprises the power controller, the method comprising the steps of:
   initializing the output energy balance amount to an initial energy;
   beginning the output of the electrical output power, when the output energy balance amount is greater than the output energy limit value or has the initial energy.

8. The method according to claim 7, wherein the output of the electrical output power is ended when the output energy balance amount is equal to zero.

9. The method according to claim 7, wherein the output energy balance amount is formed over the moving determination duration from the supplied specified generator power and the output electrical output power.

* * * * *